United States Patent [19]
Chang et al.

[11] Patent Number: 6,046,229
[45] Date of Patent: Apr. 4, 2000

[54] POLYARYL ANTITUMOR AGENTS

[75] Inventors: Ching Te Chang, Taipei; Yuh-Lin Yang, Hsin Chu Hsien, both of Taiwan

[73] Assignee: Industrial Technology Research Institute, Taiwan

[21] Appl. No.: 09/003,317

[22] Filed: Jan. 6, 1998

[51] Int. Cl.[7] .......................... A01N 43/10; C07D 49/10; C07D 333/32; C07D 333/36
[52] U.S. Cl. .......................... 514/445; 514/447; 514/448; 549/59; 549/61; 549/63
[58] Field of Search .................................. 549/59, 61, 63; 514/445, 447, 448

[56] References Cited

U.S. PATENT DOCUMENTS 5,602,170  2/1997  Chang et al. ........................... 514/244

FOREIGN PATENT DOCUMENTS

| 466094 | 7/1991 | European Pat. Off. . |
|---|---|---|
| 0 466 094 A2 | 1/1992 | European Pat. Off. . |
| 63-192687 | 1/1963 | Japan . |
| 63-161024 | 7/1963 | Japan . |
| 6-83084 | 3/1994 | Japan . |

OTHER PUBLICATIONS

Agrawal et al., "New conjugated polyanthrazolines containing thiophne moieties in the main chain," *Plastics. Manuf.*, 115:47, Abstract No. 257316s (1991).
Agrawal et al. "Synthesis and processing of heterocyclic polymers as electronic, optoelectronic, and non–linear optical materials . . . ," *Synthetic High Polymers*, 118:19, Abstract No. 102750s (1993).
Alley et al., *Cancer Res.*, 1988, 48, 589.
Baltes et al., "Model reactions on roast aroma formation. XIII. The formation of some uncommon N–heterocyclic compounds . . . ," *Food. Feed Chem.*, 118:759, Abstract No. 167795e, 1993.
Barnes et al., "Synthesis of trans, trans–1, 4–di(2–thienyl)–1, 3–butadiene," *Heterocyclic Compounds*, 71:421 Abstract No. 124096w (1969).
Beljonne et al., "Theoretical investigation of the third–order nonlinear optical properties of oligothiophenes and derivatives: Conjugation–length . . . ," *Spectroscopy*, 123:961, Abstract No. 241150n (1995).
Beny et al., "Synthesis of 3,2'–5',3"–terthiophene and other terthiophenes by the thiophencarboxaldehyde → ethynylthiophene→dithienylbutadiyne route," *Chemical Abstracts*, 96:650, Abstract No. 199454m, (1982).
Birnbaum et al., "Low lying singlet states of a,w–dithienylpolyenes: a,w–dithienylbutadiene, a,w–dithienyl––hexatriene, and a,w,–dithienylocatatetraene," *Spectroscopy*, 114:605, Abstract No. 111152t (1991).

Bohlmann et al., "Polyacetylenic compounds, 205. Constituents of the tribe Arctotideae," *Plant Biochem.*, 77:261, Abstract No. 16550e (1972).
Bohlmann et al., "Polyacetylenic compounds, 227. Synthesis of further thiophene acetylenic compounds . . . ," *Heterocycles*, 81:451, Abstract No. 63419m (1974).
Bohlman et al., "Polyaccetylenic compounds. 231. Further constituents from species of the tribus Arctotideae," *Chemical Abstracts*, 82:280, Abstract No. 152154j (1975).
Bohn et al., "Olefins," *Noncondensed Aromatics*, 81:479, Abstract No. 104960b (1974).
Boukou–Poba et al., "Formylation in an arylpyrrole series," *Chemical Abstracts*, 95:654, Abstract No. 203669j (1981).
Boukou–Poba et al., "Formylation en serie arylpyrrolique," *National Research Council of Canada*, 59:2962–2967 (1981).
Boyd, in "Principle of Practice of Oncology," Devita, Hellman, Rosenberg (eds.) vol. 3, PPO Update No. 10 (1989).
Britain et al., "Phosphonium salts and phosphoranes. Part 5. Thermal and electron–impact induced fragmentation of heteroaroylmethylenetriphenylphosphoranes," *Organometallics*, 118:929, Abstract No. 213163x (1993).

(List continued on next page.)

*Primary Examiner*—Johann Richter
*Assistant Examiner*—Dominic Keating
*Attorney, Agent, or Firm*—Fish & Richardson P.C.

[57] ABSTRACT

A compound of the formula:

$$Ar_1—B—Ar_2$$

wherein $Ar_1$ is unsubstituted or substituted phenyl, thienyl, furanyl, or pyrrolyl, in which each substituent of the substituted phenyl, substituted thienyl, substituted furanyl, and substituted pyrrolyl, independently, is aldehyde, acyl, ester, carboxyl, amido, nitrile, nitro, cyano, acetal, ketal, oxoalkyl, aminoalkyl, hydroxyalkyl, haloalkyl, iminoalkyl, acid halide, aminoalkylaminoalkyl, aminoalkylaminoalkylamino, hydroxyalkylaminoalkyl, or hydroxyalkylaminoalkylaminoalkyl; B is, —CH=CH—, or —C C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where each $R_1$, independently, is H, alkyl, or acyl; and each of $R_2$ and $R_3$, independently, is H, alkyl, hydroxyalkyl, or aminoalkyl; and $Ar_2$ is substituted phenyl, substituted thienyl, substituted furanyl, or substituted pyrrolyl, in which each substituent of the substituted phenyl, substituted thienyl, substituted furanyl, and substituted pyrrolyl, independently, is amido, nitrile, nitro, cyano, acetal, ketal, oxoalkyl, aminoalkyl, haloalkyl, iminoalkyl, acid halide, aminoalkylaminoalkyl, aminoalkylaminoalkylamino, hydroxyalkylaminoalkyl, or hydroxyalkylaminoalkylaminoalkyl; or a salt thereof. Also disclosed is a composition which contains a pharmaceutical acceptable carrier and an effective amount of a compound of the above formula.

25 Claims, No Drawings

OTHER PUBLICATIONS

Buisson et al., "Vibrational properties of poly(arylenevinylenes)," *Chemical Abstracts*, 117:30, Abstract No. 252195h, (1992).

Buschmann et al., The crystal structures of some oligomeric conjugated dithienylalkapolyenes, *Chemical Abstracts*, 89:796, Abstract No. 121194n, (1978).

Buu–Hoi, "Synthesis of 1,2–diarylethylenes by thermolysis of aldazines in liquid media," *Non–condensed Aromatic Compounds*, 69:8981, Abstract No. 96088h (1968).

Carpita et al., "One–pot palladium–catalyzed synthesis of diarylalkynes," *Heterocycles*, 101:747, Abstract No. 230281a, (1984).

Carpita et al., "Synthesis and carbon–13 NMR characterization of some π–excessive heteropolyaromatic compounds," *Chemical Abstracts*, 104:668, Abstract No. 68701a (1986).

Carre et al., "Aminosilanes in organic synthesis. Preparation of new expanded porphyrin ligands and bimetallic transition–metal complexes . . . ," *Biomolecules*, 119:847, Abstract No. 138956y (1993).

Castedo et al., "Reactivity of heteroaromatic aldehydes with low valent titanium," *Heterocycles*, 113:703 Abstract No. 231171z, (1990).

Chatani et al., "Palladium– or nickel–catalyzed reaction of alkynes with trimethylsilyl cyanide. A new synthesis of 5–aminopyrrole–2–carbonitriles," *Chemical Abstracts*, 106:738, Abstract No. 176474d, (1987).

Chem et al., "Syntheses of 1,2–bis [5–(2'–benzoxaxolyl)–pyrrole–2–yl]ethenes," *Dyes*, 123:181, Abstract No. 202023d (1995).

Chen et al., "A facile synthesis of 1,2–bis(pyrrolyl)ethylenes," *Heterocycles*, 120:959, Abstract No. 298398s (1994).

Chen et al., "Synthesis of Furan and Pyrrole–Containing α–Oligothiophenes via 1,4–diketones," *Heterocycles*, 38:1393–1398 (1994).

Chen et al., "On the chemistry of pyrrole pigments. XCIII. 1,2–bis(Dipyrrinon–9–ylidene)–ethane—a novel b–homoverdin chromophore," *Chemical Abstracts*, 124:950, Abstract No. 29496f (1996).

Cooke et al., "x–ray structure determination of several heterocyclic stilbene derivatives . . . ," *Phys. Props. Polymers*, 111:25–26, Abstract No. 40209s (1989).

Cooke, et al., "Step polymerixation via reductive coupling of dicarbonyl compounds. A fundamental study," *Chemical Abstracts*, 111:4, Abstract No. 24009w (1989).

De la Rosa et al., "Cross–coupling Reactions of Monosubstituted Acetylenes and Aryl Halides Catalyzed by Palladium on Charcoal," *Synthetic Communications*, 20:2059–2064 (1990).

D'Auria et al., "Photochemical Reactivity of Helofuran and Halothiophene Derivatives in the Presence of Arylalkenes and Arylalkynes," *J. Org. Chem.*, 55:4019–4025 (1990).

D'Auria et al., "Naturally occurring 5–[2–thienyl)ethynyl] thiopbene–2–carbaldehyde through a short synthesis of diarylacetylenes," *Chemical Abstracts*, 117:838, Abstract No. 233690z (1992).

Dority et al., "Preparation of annelated 5,10–ethanoisoquinolinium salts as neuroproctectants," *Chemical Abstracts*, 123:1206, Abstract No. 286025s (1995).

Elix et al., "Synthesis and properties of annulene polyoxides," *Chemical Abstracts*, 72:296, Abstract No. 3280p, (1970).

Freeman et al., "A novel synthesis of 2,5–diaryl–3–(phenylmethyl)thiophenes," *Heterocycles*, 119:903, Abstract No. 160013k (1993).

Freeman et al., "Reactions of Arylmethanethoils with 1,4–Disubstituted 1,3–Butadiynes," *Chemical Abstracts*, 121:1064, Abstract No. 179430g (1994).

Fu et al., "Structure/property relationship in conjugated polymers: Oxidation potentials, reduction potentials, and band gaps for a . . . ," *Phys. Props. Polymers*, 123:59, Abstract No. 297522p (1995).

Fujii et al., "Syntheses and properties of ethanediylidene–2, 2'–bis(5–dicyano–methylene–3 thiolene) and its dibromo derivatives as new extensively . . . ," *Chemical Abstracts*, 120:1082, Abstract No. 163125e (1994).

Furstner et al., "Palladium–Catalyzed Arylation of Polar Organometallics Mediated by 9–Methoxy–9–Boyabicy–clo . . . ," *Tetrahedron*, 51:11165–11176 (1995).

Galego et al., "Communication on resinification of furfural and 5–methylfurfural catalyzed by acids," *Chemical Abstracts*, 103:594, Abstract No. 87720b (1985).

Geisler et al., "Third–Order Nonlinear Optical Properties of Olgomers of Thienyleneethynylenes and Thienyl–enevinylene," *Chemical Abstracts*, 121:862, Abstract No. 216832n (1994).

Guesten et al., "Molecular orbital calculation on 1,2–difuryl– and 1,2–dithienylethylenes and their photo–cyclization products, the benzodifurans . . . ," *Chemical Abstracts*, 70:284, Abstract No. 67464t (1969).

Hinz et al., "Pyrrole studies: 34. Synthesis of 1,2–di(2–pyrolyl)ethenes and related compounds," *Heterocycles* 106:701, Abstract No. 176094e (1987).

Hoffman, et al., "Chemistry of (2– and 3–furyl)methylenes and (2– and 3– thienyl)methylenes," *Physical Org. Chem.*, 90:565, Abstract No. 22042a (1979).

Hong et al., "Theoretical Study of the Conformations and Electronic Structures of Phenylene–Pyrrole and Phenylene–Furan Copolymers," *Macromolecules*, 25:3591–3595 (1992).

Hudson et al., "Photoactive antiviral and cytotoxic activities of synthetic thiophenes and their acetylenic derivatives," *Chemical Abstracts*, 112:346, Abstract No. 154418k (1990).

Hudson et al., "Ultraviolet–mediated antibiotic activity of synthetic thiophenes and their acetylenic derivatives," *Chemical Abstracts*, 111:250, Abstract No. 189168k (1989).

Hudson et al., "Antiviral properties of acetylenes and thiophenes," *Pharmacology*, 110:16–17, Abstract No. 185340s (1989).

Hudson et al., "Antiviral properties of photosensitizers," *Radiation*, 109:352–353, Abstract No. 186415m (1988).

Irie et al., "Photochromism of diarylethenes with heterocycles rings," *Chemical Abstracts*, 116:684, Abstract No. 204189s (1992).

Jenekhe et al., "Conjugated polymer exciplexes and applications thereof," *Chemical Abstracts*, 124:52–53, Abstract No. 31099x (1996).

Jente et al,. "Formation of natural thiophene derivatives from acetylenes by Tagetes patula," *Plant Biochem.*, 96:343, Abstract No. 82768a (1982).

Jux et al., "Acetylene–cumulene–porphyrinoid," *Biomolecules*, 114:659, Abstract No. 61794f (1991).

Kagan et al., "The synthesis of 2,2':5',3"–terthiophene," *Heterocycles*, 99:629, Abstract No. 122211j (1983).

Kagan et al., "New–photodynamic (type B) phototoxic molecules," *Toxicology*, 94:177, Abstract No. 168793a (1981).

Kagan et al., "The comparison of several butadiyne and thiophene derivatives to 8–methoxypsoralen and methylene blue as singlet oxygen sensitizers," *Radiation*, 102:259, Abstract No. 2679b (1985).

Kagan et al., "The phototoxicity of some 1,3–butadienes and related thiophenes against larvae of the mosquito Aedes aegypti and of the fruit fly Drosophila . . . ," *Toxicology*, 100:169, Abstract No. 133649y (1984).

Kagan et al., "The phototoxicity of some 1,3 butadiynes and related thiophenes against larvae of the mosquito Aedes aegypti . . . ," *Agrochemicals*, 103:347–348, Abstract No. 208867r (1985).

Kanemitsu et al., Luminescence from oligothiophenes and thiophene–based oligomers, *Plastics Manuf.*, 122:58–59, Abstract No. 315842t (1995).

Kanesho Co., "Soil disinfectant composition," *Chemical Abstracts*, 96:238, Abstract No. 117583r (1982).

Kanesho Co., "Acetylene derivatives as nematocides," *Chemical Abstracts*, 96:114, Abstract No. 16085z (1982).

Karminski–Zamola et al., "Synthesis of some new 2–aryl–3–(5–substituted–2–furyl)acrylic acids," *Heterocycles* 100:581, Abstract No. 68104a (1984).

Kawai et al., "Electrochemical characteristics of poly-(trans–1,2–di(2–thienylethylene) and its battery application," *Electrochemistry*, 118:603, Abstract No. 68875z (1993).

Kawai et al., "Electrochemical properties and battery characteristics of poly(dithienylethylenes)," *Chemical Abstracts*, 119:232, Abstract No. 207023f (1993).

Kawase et al., "Synthesis of 5,6,17,18–bisdehydrotetrathia [24]annulene [2.2.2.2.]. A strained planar annulene devoid of peripheral conjugation," *Chemical Abstracts*, 123:1168, Abstract No. 340024f (1995).

Kellogg et al., "Photochemically induced cyclization of some furyl–and thienylethenes," *Phys. Org. Chem.*, 67:10161–10162, Abstract No. 107959e (1967).

Kessenikh et al., "Determination of the structure of some furan compounds according to proton magnetic resonance spectra," *Phys. Org. Chem.*, 70:247, Abstract No. 28236a (1969).

Kossmehl et al., "Electrical conductivity of partly oxidized aromatic and heteroaromatic polymers," *Phys. Prop. Polymers*, 107:27, Abstract No. 237670j (1987).

Kossmehl et al., "Liquid crystalline compounds in the thiophene series. Part 4. Azomethines and vinylenes with central azobenzene, stilbene and . . . ," *Chemical Abstracts*, 107:644, Abstract No. 68634t (1987).

Koszmehl et al., "Wittig reaction of triphenylalkylidenephosphoranes with sodium α–hydroxysulfonates," *Alicyclics*, 79:323, Abstract No. 42063j (1973).

Kossmehl et al., "Polyene–arylenes and polyene–heteroarylenes," *Chemical Abstracts*, 72:4, Abstract No. 101162w (1970).

Krasnaya et al., "Synthesis of furan compounds based on acetylenic alkoxy β–oxo esters," *Chemical Abstracts*, 67:10224, Abstract No. 108500k (1967).

Krasnaya et al., "A novel method of the synthesis of substituted furans with the use of acetylenic aloxy β–oxo esters," *Heterocyclic Compounds*, 67:6023, Abstract No. 64135p (1967).

Krkoska et al., "Furan derivatives. XVIII. Furan derivatives of ethene," *Chemical Abstracts*, 71:294, Abstract No. 3195u (1969).

Kuroda et al., "Electrophotographic photoconductor with charge transport layer containing hydrazone compound," *Radiation Chem. Photochem.*, 117:669, Abstract No. 14600e (1992).

Kuroda et al., "Thienyl group–containing hydrazone charge–transporting agent for electrophotographic photoconductor," *Radiation Chem. Photochem.*, 113:595–596, Abstract No. 123813b (1990).

Kuroda et al., "Electrophotographic properties of thiophene derivatives as charge transport material," *Radiation Chem. Photochem.*, 115:797, Abstract No. 243745u (1991).

Lapkin et al., "Synthesis of stillbenes and 1,4–diaryl–1,3–butadienes," Chemical Abstracts, 82:478, Abstract No. 111681k (1975).

Lee et al., "Aldol reactions of y– and ←methylene in 5–membered heteroaromatic compounds," *Chemical Abstracts*, 122:1038, Abstract No. 239474g (1995).

Leznoff et al., "Photocyclization reactions of aryl polyenes. VII. Photocyclization of 1–phenyl–4–thienyl–and 1,4–dithienyl–1,3–butadienes," *Chemical Abstracts*, 80:424, Abstract No. 145938y (1974).

Lucchesini, "A Simple Way to Sequentially Connected Polycycles Containing Terminal Pyrrole Rings: Synthesis of Possible Precursors of Materials for Nonlinear Optics," *Tetrahedron*, 48:9951–9966 (1992).

Lund et al., "Electrochemical reduction of furan derivatives derived from biomass," *Chemical Abstracts*, 105:614, Abstract No. 97262j (1986).

Maas et al., "The heteroaromatic Cope rearrangement of 1–pyridyl–, 1–furyl–, and 1–thieny–2–vinylcyclo–propanes," *Phys. Org. Chem.*, 94:617, Abstract No. 120606q (1981).

Maerkl et al., "Tetraoxz[22]porphyrin(2.2.2.2.) dication and tetraoxa[24]porphyrinogen(2.2.2.2)," *Biomolecules*, 121:1055, Abstract No. 179353j (1994).

Manecke et al., "Syntheses, spectroscopic behavior and electrical conductivity of some oligomeric unsymmetrically disubstituted thienylenevinylenes," *Chemical Abstracts*, 78:464, Abstract No. 124380d, (1973).

Marani et al., "New synthesis method of polythiophenes," *Chemical Abstracts*, 122:13, Abstract No. 10870k (1995).

Marchant et al., "Polyacetylenes in Hawaiian Bidens," *Biochemicsl Systematics and Ecology*, 12:167–178 (1984).

Marles et al., "Thiophenes as Mosquito Larvicides: Structure–Toxicity Relationship Analysis," *Biochemistry and Physiology*, 41:89–100 (1991).

Martinez et al., "Electrochemical synthesis and optical analysis of poly(2,2'dithienyl)–5,5'–diylvinylene," *Chemical Abstracts*, 109:24, Abstract No. 38585b (1988).

Mitsuhara et al., "Electrochemical preparation of poly(di(2–thienyl)benzene)s and poly(4,4'–di(2–thienyl)bi–phenyl)," *Makromol. Chem.*, 189:1755–1763 (1988).

Montheard et al., "Preparation of 1,2–bis(2–thienylethene, 2,4–bis(2–thienyl)pyrimidine and 3,6–bis(2–thienyl–pyridazine," *Heterocycles*, 104:696–697 (1986).

Naarmann et al., "Thienylphenylenes, their preparation, and use in preparing electrically conductive polymers," *Chemical Abstracts*, 120:1034, Abstract No. 217259x (1994).

Nakamura et al., "Thermally irreversible photochromic systems, a theoretical study," *Radiation Chem. Photochem.*, 111:703, Abstract No. 205160j (1989).

Nakayama et al., Preparation of (E)–1,2–bis(2,2'–bithiophene–5–yl)ethylene and (E)–1,2,–bis(2,2':5',2"–terthiophene–5–yl)ethylene, *Heterocycles*, 106:666–667, Abstract No. 138187e (1987).

Nakayama et al., "Tetra–2–thienyl– and tetrakis(5,2'–bithiophen–2–yl)thiophenes and –selenophenes," *Chemical Abstracts*, 117:670–671, Abstract No. 251168q (1992).

Nakayama et al., Preparation of a series of oligo[thiophene–2.5 diyl]vinylenes, *Chemical Abstracts*, 115:878, Abstract No. 11429x (1991).

Nakayama et al., "Reactions of elemental sulfur and selenium with some acetylenic compounds. Formation of thiophenses and selenophases," *Chemical Abstracts*, 108:722, Abstract No. 131471a (1990).

Natarajan et al., "Optical limiting in solutions of dithienyl polyenes," *Chemical Abstracts*, 120:900, Abstract No. 203720d (1994).

Nawwar et al., "Cyclohex–2–en–1–ones in heterocyclic synthesis: facile synthesis of 5,6–dihydrocoumarins, their thio analogs and their corresponding . . . ," *Heterocycles*, 118:829, Abstract No. 101764n, (1993).

Oagawa et al., "Synthesis of [16]annulenone 4,7:10–13–dioxides and aromatic 4,7:10,13–dioxid[15]annulenium cations. Novel 14π odd annulene systems," *Heterocycles*, 81:535–536, Abstract No. 120594r (1974).

Ogawa et al., "Synthesis of [16]annulene 1,4:7,10–dioxide and the verification of an induced paramagnetic ring current . . . ," *Heterocycles*, 78:383, Abstract No. 136253c (1973).

Ogawa et al., "A simple methodology for azaannulene synthesis preparation and properties of 2,15–diethoxy–carbonyl–4,7:10,12–diepoxy–2–cis,8–cis . . . ," *Heterocycles*, 101:643, Abstract No. 72709q (1984).

Ogawa et al., "Oxygen–bridged thia[15]annulenes: demonstration of a strong paramagnetic ring current in a 4nπ–thiannulene (n=4)," *Heterocycles*, 98:5558, Abstract No. 89336h (1983).

Ogawa et al., "Higher homologs of cycloheptatriene, tropylium ion, and oxepin. Demonstration of a diamagnetic and paramagnetic ring current in novel . . . ," *Chemical Abstracts*, 79:374, Abstract No. 17664y (1973).

Ogawa et al., "Preparation of oxygen–bridged aza[15]–and aza[17] annulene dicarboxylates by intramolecular azide cyclization," *Heterocycles*, 108:707, Abstract No. 186726t (1988).

Ogawa et al., "Bridging effects of furan ring incorporated in the perimeters of a bisdehydro[16]annulene and a bisdehydro[18]annulene: syntheses of . . . ," *Heterocycles*, 91:608–609, Abstract No. 39215c, (1979).

Onoda et al., "Electrochemical preparation of conducting poly=(trans–1,2–di(2–thienyl)ethylene) and poly (1,4–di(2–thienyl)–1,3–butadiene) . . . ," *Chemical Abstracts*, 116:606, Abstract No. 29974v (1992).

Papadopoulos et al., "Analysis of the polarizability and second hyperpolarizability of a,w–dithienylopolyenes," *Chemical Abstracts*, 123:880, Abstract No. 21193p (1995).

Parkanyi et al., "Bond lengths and bond orders in π–electron heterocycles," *Chemical Abstracts*, 88:678, Abstract No. 189788u (1978).

Pennanen et al., "Studies on the furan series. Part VII. A preparation of 2,3–di(2–furyl and thienyl) furans," *Chemical Abstracts*, 88:514, Abstract No. 136386e (1978).

Piqueras et al., "Structural and electronic properties of oligomeric heteroarylene vinylenes: a theoretical approach," *Chemical Abstracts*, 120:38, Abstract No. 135672n (1994).

Reimlinger et al., "Transformation of aromatic ketones into ethynyl derivatives," *Condensed Aromatic Compounds*, 71:347, Abstract No. 91149k, (1969).

Reisch et al., "Microbiological activity of simple acetylene compounds," *Chemical Abstracts*, 67:8310, Abstract No. 8843m (1967).

Reynolds et al., "Substituent Effects on the Electrical Conductivity and Electrochemical Properties of Conjugated Furanyl Phenylene Polymers," *Macromolecules*, 26:2095–2103 (1993).

Reynolds et al., "Poly(1,4–bis(pyrrol–2–yl)phenylene): A New Electrically Conducting and Electroactive Polymer Containing the Bipyrrole–Phenylene Repeat Unit," *Macromolecules*, 27:7225–7227 (1994).

Ribereau et al., Compounds containing three separated benzene and thiophene rings, *Heterocycles*, 77:479, Abstract no. 61709z (1972).

Rossi et al., "A palladium–promoted route to 3–alkyl–4–(1–alkynyl)hexa–1,5–dyn–3–enes and/or 1,3–diynes," *Chemical Abstracts*, 102:524, Abstract No. 184442z, (1985).

Rossi et al., "Palladium–catalyzed syntheses of naturally occurring acteylenic thiophenes and related compounds," *Biomolecules*, 102:575, Abstract No. 78635e, (1985).

Rudenko et al., "Determination of thermodynamic parameters of the dissolution of some unstable compounds by a gas–liquid chromatographic method," *Thermodynamics and Thermochemistry*, 74:325, Abstract No. 116717w, 1971.

Ruiz et al., "Electrically Conducting Polymers Containing Substituted Phenylene and Heterocycle Repeat Units," *Synthetic Metals*, 41–43:783–788 (1991).

Saigo et al., "Preparation, chrioptical properties, and chiral recognition ability of carbamoylated polyamides having (")–anti head–to–head coumarin . . . ," *Chemical Abstracts*, 111:4, Abstract No. 24003q (1989).

Saikachi et al., "Synthesis of furan derivatives. LV. Macrocyclic rings from the reaction of dialdehydes with bisphosphoranes and with diamines," *Heterocyclic Compounds*, 75:489–490, Abstract No. 5870s (1971) Abstract No. 6798t (1993).

Sarkar et al., "Diacetylenes with formally conjugated side groups: precursors to liquid–crystalline polymers?," *Chemical Abstracts*, 117:1, Abstract No. 192371a (1992).

Sarkar et al., "Solid–state and electrochemical polymerization of novel diacetylene monomers," *Chemical Abstracts*, 115:7, Abstract No. 93047b (1991).

Sawada et al., "Preparation of tetraarylthiophenes and tetraarylselenophenes by reactions of diarylacetylenes with elemental sulfur and selenium," *Chemical Abstracts*, 119:1116, Abstract No. 95689u, (1993).

Schroedter et al., "Pyrolysis of colored low molecular weight Mailard products," *Food. Feed. Chem.*, 120:973, Abstract No. 161956c (1994).

Shapiro et al., "1–(–2'–Furyl)–2–(2'–formyl–5"–furyl)ethylene or its methyl derivative as an intermediate for the synthesis of furan–2,5–dicarboyxlic acid," *Heterocycles*, 91:479, Abstract No. 5104a (1979).

Shapiro et al., "Mass–spectrometric study of derivatives of furan and 1,2–di–(2–furyl)ethylene," *Chemical Abstracts*, 98:576, Abstract No. 224736f (1983).

Shapiro et al., "Reactions of aldehydes of furan series. I. New method for preparation of 1,2–bis(2–furyl) ethylene derivatives," *Chemical Abstracts*, 88:478, Abstract No. 37532t (1978).

Shapiro et al., "Synthesis and study of the properties of condensation products of furan compounds with oxo compounds," *Chemical Abstracts*, 84:474, Abstract No. 135390g (1976).

Spangler et al., "The design of new copolymers for $x^{(3)}$ [third–order susceptibility] applications," *Synthetic High Polymers*, 118:7, Abstract No. 39527g (1993).

Tomiuchi et al., "Organic thin–film electroluminescent device having thienyl derivative light–emitting layer," *Spectroscopy*, 122:839, Abstract No. 302601p (1995).

Tormos et al., "Poly(2,5–thienylene ethynylene) and related oligomers," *Chemical Abstracts*, 118:38, Abstract No. 214067f, (1993).

Weghorn et al., "[22]Dehydropentaphyrin–(2.1.0.0.1) and [22]pentaphyrin–(2.1.0.0.1): novel sapphyrin analogs," *Chemical Abstracts*, 123:1082, Abstract No. 111718t (1995).

Yamada et al., "Electrically conducting polymers," *Synthetic High Polymers*, 116:15, Abstract No. 42264h (1992).

Yom–Tov et al., "Heterocyclic fused tropylium ions. I. Synthesis of dithienocycloheptanones," *Heterocycles*, 78:469, Abstract No. 97519x (1973).

Yufit et al., "Relations between chromatographic retention indexes and thermodynamic dissolution parameters," *Chemical Abstracts*, 72:290–291, Abstract No. 16223x (1970).

Zimmerman et al., "Concentration effects in photochemical cis–transisomerization. Difurylethylene and dithienylethylene," *Phys. Org. Chem.*, 70:283, Abstract No. 57004d (1969).

POLYARYL ANTITUMOR AGENTS

BACKGROUND OF THE INVENTION

Surpassed only by heart disease, cancer is the second leading cause of death in the United States. Estimated by the American Cancer Society, approximately 4 million people have died from cancer since the turn of this decade. The types of cancer treatments usually include chemotherapy, surgery, radiation, hormones, and immunotherapy. Chemotherapy continues to be a powerful treatment, especially for cancers that are in inoperable or metastatic forms.

Many aryl-containing compounds have been reported to possess cytotoxic activities, e.g., 2-aryl-1,8-naphthyridin-4 (1H)-ones (Chen et al., J. of Med. Chem. 1997, 40(19), 3049–56), 3-aryl-substituted oxatriazole-5-imine derivatives (Vilpo et al., Anti-Cancer Drug Design, 1997, 12(2), 75–89), and 1,2-dihydropyrido[3,4-b]pyrazines (Temple et al., J. of Med. Chem. 1987, 30(10), 1746–51).

SUMMARY OF THE INVENTION

An aspect of the present invention relates to a polyaryl compound (i.e., a compound that has at least two aryl groups) of the following formula:

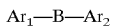

wherein $Ar_1$ is unsubstituted phenyl, thienyl, furanyl, or pyrrolyl; B is

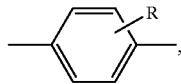

—CH=CH—, or —C≡C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where each R$_1$, independently, is H, alkyl, or acyl; and each of R$_2$ and R$_3$, independently, is H, alkyl, hydroxyalkyl, or aminoalkyl; and Ar$_2$ is substituted phenyl, substituted thienyl, substituted furanyl, or substituted pyrrolyl, in which each substituent of substituted phenyl, substituted thienyl, substituted furanyl, and substituted pyrrolyl, independently, is amido, nitrile, nitro, cyano, acetal, ketal, oxoalkyl, aminoalkyl, haloalkyl, alkyliminoalkyl, acid halide, aminoalkylaminoalkyl, aminoalkylaminoalkylamino, hydroxyalkylaminoalkyl, or hydroxyalkylaminoalkylaminoalkyl; or a salt thereof. Such a salt can be formed, between a counterion of an ionizable group of a polyaryl compound of the formula described above. For example, a sodium salt of a polyaryl compound can be formed between a sodium ion and a carboxyl group of that compound.

One subset of the compounds covered by the above formula are featured by that B is

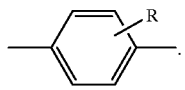

Preferably, each substituent of substituted phenyl, substituted thienyl, substituted furanyl, and substituted pyrrolyl, independently, is oxoalkyl, aminoalkyl, haloalkyl, hydroxyalkylaminoalkyl, or hydroxyalkylaminoalkylaminoalkyl. The term "substituted" in this disclosure is defined as having one substituent on the referred structure and the position of this substituent is specified, except in cases when the referred structure is a substituted phenyl, of which the position of a substituent can be any of the five unoccupied positions.

Another subset of the compounds covered by the above formula are featured by that B is —CH=CH—. Preferably, each substituent of substituted phenyl, substituted thienyl, substituted furanyl, and substituted pyrrolyl, independently, is oxoalkyl, aminoalkyl, haloalkyl, hydroxyalkylaminoalkyl, or hydroxyalkylaminoalkylaminoalkyl.

Still another subset of the compounds covered by the above formula are featured by that B is —C≡C—. Preferably, each substituent of substituted phenyl, substituted thienyl, substituted furanyl, and substituted pyrrolyl, independently, is oxoalkyl, aminoalkyl, haloalkyl, hydroxyalkylaminoalkyl, or hydroxyalkylaminoalkylaminoalkyl.

A further aspect of the present invention relates to polyaryl compounds also covered by the same above formula, wherein Ar$_1$ is substituted phenyl, substituted thienyl, substituted furanyl, or substituted pyrrolyl, in which each substituent of substituted phenyl, substituted thienyl, substituted furanyl, and substituted pyrrolyl, independently, is aldehyde, acyl, ester, carboxyl, amido, nitrile, nitro, cyano, acetal, ketal, oxoalkyl, aminoalkyl, hydroxyalkyl, haloalkyl, alkyliminoalkyl, acid halide, aminoalkylaminoalkyl, aminoalkylaminoalkylamino, hydroxyalkylaminoalkyl, or hydroxyalkylaminoalkylaminoalkyl;

B is

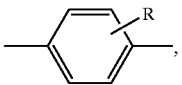

—CH=CH—, or —C≡C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where R$_1$ is H, alkyl, or acyl; and each of R$_2$ and R$_3$, independently, is H, alkyl, hydroxyalkyl, or aminoalkyl; and Ar$_2$ is

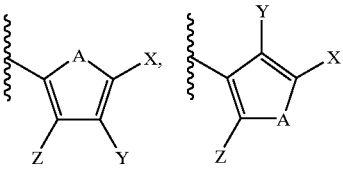

or substituted phenyl; in which A is nitrogen, oxygen, or sulfur; X is carboxyl, amido, nitrile, nitro, cyano, acetal, ketal, oxoalkyl, aminoalkyl, hydroxyalkyl, haloalkyl, acid halide, aminoalkylaminoalkyl, aminoalkylaminoalkylamino, hydroxyalkylaminoalkyl, or hydroxyalkylaminoalkylaminoalkyl; Y is aldehyde, acyl, ester, carboxyl, amido, nitrile, nitro, cyano, acetal, ketal, oxoalkyl, aminoalkyl, hydroxyalkyl, haloalkyl, alkyliminoalkyl, acid halide, aminoalkylaminoalkyl, aminoalkylaminoalkylamino, hydroxyalkylaminoalkyl, or hydroxyalkylaminoalkylaminoalkyl; Z is acyl, ester, carboxyl, amido, nitrile, nitro, cyano, acetal, ketal, oxoalkyl, aminoalkyl, hydroxyalkyl, haloalkyl, alkyliminoalkyl, acid halide, aminoalkylaminoalkyl, hydroxyalkylaminoalkyl, or hydroxyalkylaminoalkylaminoalkyl; and each substituent of substituted phenyl, independently, is aldehyde, acyl, ester, carboxyl, amido, nitrile, nitro, cyano, acetal, ketal, oxoalkyl, aminoalkyl, hydroxyalkyl, haloalkyl, alkyliminoalkyl, acid halide, aminoalkylaminoalkyl, aminoalkylaminoalkylamino, hydroxyalkylaminoalkyl, or hydroxyalkylaminoalkylaminoalkyl or a salt thereof.

A subset of the above-described compounds are featured by that B is

Preferably, each substituent of substituted phenyl, substituted thienyl, substituted furanyl, and substituted pyrrolyl assigned to $Ar_1$, independently, is oxoalkyl, aminoalkyl, haloalkyl, hydroxyalkylaminoalkyl, or hydroxyalkylaminoalkylaminoalkyl. More preferably, $Ar_2$ is

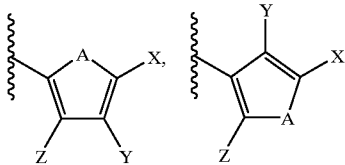

or substituted phenyl; in which each of X and Z, independently, is hydroxyalkyl; Y is aldehyde, or hydroxyalkyl; and each substituent of said substituted phenyl, independently, is aldehyde, or hydroxyalkyl.

Another subset of the above-described compounds are featured by that B is —CH═CH—. Preferably, each substituent of substituted phenyl, substituted thienyl, substituted furanyl, and substituted pyrrolyl assigned to $Ar_1$, independently, is oxoalkyl, aminoalkyl, haloalkyl, hydroxyalkylaminoalkyl, or hydroxyalkylaminoalkylaminoalkyl. More preferably, $Ar_2$ is

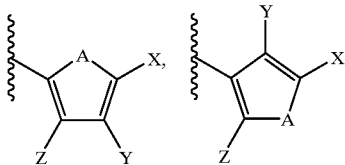

or substituted phenyl; in which each of X and Z, independently, is hydroxyalkyl; Y is aldehyde, or hydroxyalkyl; and each substituent of said substituted phenyl, independently, is aldehyde, or hydroxyalkyl.

Yet another subset of the above-described compounds are featured by that B is —C≡C—. Preferably, each substituent of substituted phenyl, substituted thienyl, substituted furanyl, and substituted pyrrolyl assigned to $Ar_1$, independently, is oxoalkyl, aminoalkyl, haloalkyl, hydroxyalkylaminoalkyl, or hydroxyalkylaminoalkylaminoalkyl. More preferably, $Ar_2$ is

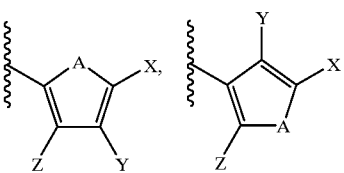

or substituted phenyl; in which each of X and Z, independently, is hydroxyalkyl; Y is aldehyde, or hydroxyalkyl; and each substituent of said substituted phenyl, independently, is aldehyde, or hydroxyalkyl.

A still another aspect of this invention relates to an asymmetric compound of the described formula, supra, wherein each of $Ar_1$ and $Ar_2$, independently, is substituted phenyl, substituted pyrrolyl, substituted furanyl, or substituted thienyl, in which each substituent of substituted phenyl, substituted pyrrolyl, substituted furanyl, or substituted thienyl, independently, is acetal, ketal, oxoalkyl, hydroxyalkyl, aminoalkyl, alkyliminoalkyl, acyl, carboxyl, ester, amide, acid halide, nitrile, or hydroxyalkylaminoalkylaminoalkyl; and B is

—C═CH—, or —C≡C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where R$_1$ is H, alkyl, or acyl; each of R$_2$ and R$_3$, independently, is H, alkyl, hydroxyalkyl, or aminoalkyl; or a salt thereof.

A subset of the above-described compounds are featured by that each substituent of $Ar_1$ and $Ar_2$, independently, is aldehyde, alkoxy, hydroxyalkyl, acyl, or ester; or a salt thereof.

Another subset of the above-described compounds are featured by that each substituent of $Ar_1$ and $Ar_2$, independently, is aldehyde or hydroxyalkyl; or a salt thereof.

Yet still another aspect of the present invention relates to a pharmaceutical composition which contains a pharmaceutically acceptable carrier and an effective amount of at least one of the polyaryl compounds of the above-mentioned formula, wherein each of $Ar_1$ and $Ar_2$, independently, is pyrrolyl, substituted pyrrolyl, furanyl, substituted furanyl, thienyl, substituted thienyl, phenyl, or substituted phenyl, in which each substituent of substituted pyrrolyl, substituted furanyl, substituted thienyl, or substituted phenyl, independently, is aldehyde, acyl, ester, carboxyl, amido, nitrile, nitro, cyano, acetal, ketal, oxoalkyl, aminoalkyl, hydroxyalkyl, haloalkyl, alkyliminoalkyl, acid halide, aminoalkylaminoalkyl, aminoalkylaminoalkylamino, hydroxyalkylaminoalkyl, or hydroxyalkylaminoalkylaminoalkyl; and B is

—C═CH—, or —C≡C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where R$_1$ is H, alkyl, or acyl; and each of R$_2$ and R$_3$, independently, is H, alkyl, hydroxyalkyl, or aminoalkyl.

A subset of the compounds that can be used in the above-described pharmaceutical composition are featured by that each substituent of Ar$_1$ and Ar$_2$, independently, is aldehyde or hydroxyalkyl.

The term "alkyl" in this disclosure denotes a straight or branched hydrocarbon chain containing 1 to 8 carbon atoms, or cyclic hydrocarbon moieties containing 3 to 8 carbon atoms. Examples of alkyl include, but are not limited to, methyl, ethyl, propyl, isopropyl, butyl, isobutyl, sec-butyl, tert-butyl, amyl, isopentyl, hexyl, isohexyl, heptyl, octyl, cyclopropyl, cyclopentyl, cyclohexyl, cycloheptyl, adamantyl, norbornyl, isobornyl, cyclohexylmethyl, 1- or 2-cyclohexylethyl, and 1-, 2-, or 3-cyclohexylpropyl. "Halo" or "halide" in this disclosure refers to fluoro, chloro, bromo, and iodo. Either ends of the amido, ester, and cyano moieties can be connected to a polyaryl compound. For example, an amido moiety can bond to the rest of the compound via the nitrogen end (—NH—CO—R') or the carbon end (—CO—NH—R'), whereas R' denotes an alkyl group here. The substitution pattern of B as a phenylene herein may be para, meta, or ortho. The term "substituted" in this disclosure is defined as mono-substituted. As used herein, an "asymmetric" polyaryl compound is meant a substituent of Ar$_1$ cannot be identical to that of Ar$_2$ of that compound.

Other features and advantages of the present invention will be apparent from the following description of the preferred embodiments, and also from the appending claims.

DETAILED DESCRIPTION OF THE INVENTION

The polyaryl antitumor compounds described above can be prepared by methods well known in the art. For example, a dihalo-substituted polyaryl ethylene compounds can react with an excess amount of a suitable nucleophile that possesses a formyl moiety, e.g., dimethylformamide, and by nucleophilic substitution, to produce the corresponding product, e.g., diformyl polyaryl ethylene compounds. As another example, diformyl polyaryl acetylene derivatives can be synthesized by first reacting a properly activated acetylene core, e.g., copper trimethylsilyl acetylide, with a catalyzed furan, pyrrole, or thiophene that is substituted with a formyl group, e.g., a palladium catalyzed formyl thiophene, by reductive elimination. This substituted monoaryl acetylene can further react with another catalyzed substituted thiophene to afford the desired diformyl substituted product. See Sonogashira et al., Tetrahedron Lett. 1975, 4467. Still another example, diformyl polyaryl phenylene derivatives can be prepared by coupling dihalo-substituted phenylene with two equivalents of a properly substituted furan, thiophene, or pyrrole, e.g., formyltributylstannyl thiophene, to synthesize the desired product. These above-mentioned diformyl substituted compounds can be further reduced by sodium borohydride to form the corresponding hydroxyalkyl derivatives. On the other hand, these diformyl-substituted polyaryl derivatives can also undergo reductive amination with the properly substituted amines and sodium borohydride to produce the corresponding hydroxyalkylaminoalkyl or hydroxyalkylaminoalkylaminoalkyl substituted polyaryl derivatives.

Other than various polyaryl compounds described above which can be used to treat tumors (e.g., leukemia, lung cancer, colon cancer, CNS cancer, melanoma, ovarian cancer, renal cancer, prostate cancer, and breast cancer), a method of treating tumor by administering to a patient the above-mentioned composition is also contemplated as an aspect of this invention. Within this invention too is the use of polyaryl compounds for the manufacture of a medicament for the treatment of tumor.

As used herein, an effective amount of formulation is defined as the amount of the polyaryl compound which, upon administration to a patient in need, inhibits growth of tumor cells, kills malignant cells, or reduces the size of the tumors, or otherwise confers a therapeutic effect on treated patient. The effective amount to be administered to a patient is typically based on body surface area, patient weight, and patient condition. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. An effective amount of a polyaryl compound used to practice the invention can range from about 5 mg/kg to about 50 mg/kg. Effective doses will also vary, as recognized by those skilled in the art, dependant on route of administration, excipient usage, and the possibility of co-usage with other therapeutic treatments including use of other antitumor agents and radiation therapy.

The pharmaceutical composition may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

The above-mentioned polyaryl compounds can also be formulated into dosage forms for other routes of administration utilizing well-known methods. The pharmaceutical composition can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with the conventional procedure by compressing mixtures of the active polyaryl compound and a solid carrier, and a lubricant. Examples of solid carriers include starch and sugar bentonite. The polyaryl compound can also be administered in a form of a hard shell tablet or capsule containing, for example, lactose or mannitol as a binder and a conventional filler and a tableting agent.

The antitumor activity of polyaryl compounds described above can be preliminarily evaluated using an in vitro assay, and then confirmed by in vivo testing. For example, the polyaryl compounds can be evaluated by a microculture assay using 3-(4,5-dimethylthiazol-2-yl)2,5-diphenyltetrazolium bromide ("MTT") [Boyd, in "Principle of Practice of Oncology," Devita, Hellman, Rosenberg (eds.) Vol. 3, PPO Update, No. 10, 1989] for in vitro cytotoxicity. The MTT assay is based on the production of a dark blue formazan product by dehydrogenase in the mitochondria of live tumor cells after exposure to drug for 6 days [Alley, et al., Cancer Res. 1988, 48, 589]. Thus, only live cells are stained and can be measured at 570 nm. Antitumor cytotoxicity is reported as IC$_{50}$, effect drug dose at which cell growth is retarded to 50% of control culture of tumor cells.

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever, All publications recited herein, including patents, are hereby incorporated by reference in their entirety.

EXAMPLE 1

(Synthesis of 1,2-bis[2-(5-formyl)-thienyl]acetylene)

In a 100-ml flask was placed 20 ml of benzene and 1.12 g (5 mmol) of 2-formyl-5-iodothiophene. To this stirred mixture was added 0.98 g (10 mmol) of (trimethylsilyl) acetylene, 600 mg of tetrakis (triphenylphosphine) palladium, 160 mg of copper(I) iodide, 120 mg of triethylbenzyl ammonium chloride (TEBAC), and 20 ml of 2.5 N deoxygenated KOH. The mixture was stirred at 40° C. for 48 hrs. After cooled to room temperature (r.t.), saturated ammonium chloride solution was added and the mixture was stirred for 0.5 hr and the resulted precipitation was filtered off. The filtrate was extracted with ether. The organic extract was washed with saturated sodium bicarbonate and brine, and then dried with anhydrous $MgSO_4$. After filtered and concentrated, the residue was chromatographed with silica gel column (eluted with EtOAc/n-hexane) to yield 0.34 g (58% yield) of product (mp 154° C.). $^1H$ NMR ($CDCl_3$): δ7.39 (d, 2H, J=4.2 Hz), 7.69 (d, 2H, J=4.2 Hz), 9.89 (S, 2H, CHO). MS (m/z): 246 (M$^+$, 100), 245 (85.08), 173 (12.29). IR (Kbr, cm$^{-1}$): 1655.

EXAMPLE 2

(Synthesis of 1,2-bis[2-(5-hydroxymethyl)-thienyl] acetylene)

1,2-bis[2-(5-formyl)-thienyl]acetylene (3 mmol) was dissolved in 30 ml of ethanol and treated with 1 mmol of sodium borohydride. After stirred at r.t. for 4 hrs, water was added to quench the reaction. The mixture was extracted with ether. The organic extract was washed with saturated sodium bicarbonate and brine, and dried with $MgSO_4$. Filtration and concentration afforded almost quantitative yield of 1,2-bis[2-(5-hydroxymethyl)-thienyl]acetylene. 1,2-bis[2-(5-hydroxymethyl)-thienyl]acetylene (mp 146~147° C.): $^1H$ NMR (DMSO-$d_6$): δ4.63 (d, 4H, J=6 Hz), 5.66 (t, 4H, J=6 Hz), 6.92 (t, 2H), 7.26 (d, 2H, J=3.9 Hz). MS (m/z): 250 (M$^+$, 100), 233 (39.64), 69 (16.34). IR (KBr, cm$^{-1}$): 3350, 3279, 2908, 2863, 1021.

EXAMPLE 3

Synthesis of (E)-1,2-bis[2-(5-formyl)-thienyl]ethene

In a 25-ml flask was placed 5 ml of DMF and 0.16 ml (1.74 mmol) of phosphorous oxychloride. The mixture was stirred at ice-bath for 0.5 hr. The mixture was then treated with 303 mg (1.58 mmol) of (E)-1-2-bis(2-thienyl)ethene and stirred at 50° C. for 48 hrs. After the temperature dropped to r.t., 10 ml of 10% sodium bicarbonate was added and the mixture was extracted with $CH_2Cl_2$. The organic extract was washed with brine and dried with anhydrous $MgSO_4$. After filtered and concentrated, the residue was chromatographed with silica gel column (eluted with EtOAc/n-hexane) to yield 0.04 g of bis-formyl derivative. Recrystallization of bis-formyl derivative form EtOAc afforded 0.03 g (6% yield) of pure product. (E)-1,2-bis[2-(5-formyl)-thienyl]ethene (mp 209° C.): $^1H$ NMR ($CDCl_3$): δ7.21~7.26 (m, 4H), 7.69 (d, 2H, J=4.2 Hz), 9.89 (s, 2H). MS (m/z): 248 (M$^+$, 77.70), 247 (46.04), 147 (40.65), 69 (100). IR (KBr, cm$^{-1}$): 2924, 2850, 1651.

EXAMPLE 4

Synthesis of (E)-1,2-bis[2-(5-hydroxymethyl)-thienyl] ethene (E)-1,2-bis[2-(5-formyl)-thienyl]ethene (3 mmol) was dissolved in 30 ml of ethanol and treated with 1 mmol of sodium borohydride. After stirred at r.t. for 4 hrs, water was added to quench the reaction. The mixture was extracted with ether. The organic extract was washed with saturated sodium bicarbonate and brine, and dried with $MgSO_4$. Almost quantitative yield of the corresponding hydroxymethyl derivative resulted after filtration and concentration. (E)-1,2-bis[2-(5-hydroxymethyl)-thienyl]ethene (mp 133~134° C.): $^1H$ NMR (DMSO-$d_6$): δ4.57 (br, 4H), 5.49 (br, 2H), 6.84 (d, 2H, J=2.7 Hz), 6.98~7.01 (m, 4H). MS (m/z): 252 (M$^+$, 100), 235 (52.06), 83 (65.98), 81 (30.41), 73 (34.54), 71 (74.23), 69 (72.16). IR (KBr, cm$^{-1}$): 3265, 2918, 2860, 1013.

EXAMPLE 5

Synthesis of (E)-1-(2-thieny)-2-{2-[5-(aminomethyl)]-thienyl}ethene (i) In a 25-ml flask was placed 2.22 g (10 mmol) of (E)-1-(2-thienyl)-2-[2-(5-hydroxymethyl)thienyl]ethene, 1.62 g (11 mmol) of phthalimide, 2.89 g (11 mmol) of triphenylphosphine and 20 ml of tetrahydrofuran. To this mixture was slowly added 1.92 g (11 mmol) of diethyl azodicarboxylate and stirred at r.t. for 24 hrs. Water was added to quench the reaction. The mixture was extracted with ether. The organic extract was washed with saturated sodium bicarbonate and brine, and dried with anhydrous $MgSO_4$. After filtered and concentrated, the residue was chromatographed with silica gel column (eluted with EtOAc/n-hexane) to afford 2.22 g (64% yield) of pure product (mp 160° C.). $^1H$ NMR ($CDCl_3$): δ4.97 (s, 2H), 6.83 (d, 1H, J=3.9 Hz), 6.94~7.17 (m, 6H), 7.70~7.73 (m, 2H), 7.85~7.88 (m, 2H). MS (m/z): 351 (M$^+$, 100), 203 (20.95), 171 (17.61). IR (KBr, cm$^{-1}$): 1769, 1702, 1609.

(ii) (E)-1-(2-thieny)-2-{2-[5-(N-phthalimidomethyl)]-thienyl}ethene (0.35 g, 1 mmol) was dissolved in 5 ml of ethanol and treated with 0.055 g (1.1 mmol) of 80% hydrazine while heating at 60° C. The mixture was heated at reflux for 4 hrs and then concentrated at reduced pressure. The residue was treated with 7 ml of 0.5 N HCl and the resulted precipitation was filtered off. The filtrate was added 1 N NaOH till pH>12 and then extracted with chloroform. The organic extract was washed with brine and dried with anhydrous $MgSO_4$. After filtered and concentrated, 0.18 g (83% yield) of product (mp 89~90° C.) was obtained. $^1H$ NMR ($CDCl_3$): δ4.01 (s, 2H), 6.78 (d, 1H, J=4.8 Hz), 6.86 (d, 1H, J=3.3 Hz), 6.98~7.02 (m, 4H), 7.17 (d, 1H, J=4.8 Hz). MS (m/z): 221 (M$^+$, 100), 205 (48.94). IR (KBr, cm$^{-1}$): 3352, 3264, 3067, 3010, 2919, 2851, 1573.

EXAMPLE 6

Synthesis of (E)-1-(2-thieny)-2-[2-{5-[N-(2-hydroxyethyl) aminomethyl]}thienyl]ethene In a 100-ml flask was placed 30 ml of methanol, 10 mmol of ethanolamine, and a few drops of acetic acid. (E)-1-(2-thieny)-2-[2-(5-formyl)thienyl]ethene (1.10 g, 5 mmol) was added slowly at r.t. The reaction was monitored by TLC until the formyl-containing compound was consumed. Excess sodium borohydride was added and the reaction again was monitored by TLC until the imine intermediate disappeared. The mixture was concentrated under reduced pressure and the residue was treated with 50 ml of EtOAc and 50 ml of 0.1 N HCl. The resulting precipitation was filtered and the filtrate was washed with EtOAc. After combined with the precipitation, the filtrate was treated with 2 N NaOH till pH>12 and then extracted with EtOAc. The organic extract was washed with saturated sodium bicarbonate and brine, and dried with anhydrous MgSO$_4$. After the reaction mixture was filtered and concentrated, 1.30 g of (E)-1-(2-thieny)-2-[2-{5-[N-(2-hydroxyethyl)aminomethyl]}thienyl]ethene was produced. Recrystallization with n-hexane afforded 1.22 g of the desired product. (E)-1-(2-thienyl)-2-[2-{5-[N-(2-hydroxyethyl)-aminomethyl]}-thienyl]ethene (mp 91° C.): $^1$H NMR (CD$_3$Cl$_3$): δ2.09 (br, 2H), 2.84 (t, 2H, J=4.9 Hz), 3.67 (d, 1H, J=4.9 Hz), 3.97 (s, 2H), 6.79 (d, 1H, J=3.3 Hz), 6.86 (d, 1H, J=3.6 Hz), 6.97~7.02 (m, 4H), 7.17 (d, 1H, J=4.8 Hz). MS (m/z): 265 (M$^+$, 29.52), 205 (100), 85 (46.99), 83 (28.16), 71 (59.04), 69 (32.83). IR (KBr, cm$^{-1}$): 3128, 3100, 3066, 3027, 2920, 2851.

EXAMPLE 7

(E)-1-(2-thienyl)-2-[2-(5-(N-(2-aminoethyl)aminomethyl)) thienyl]ethene

In a 100-ml flask was placed 30 ml of methanol, 10 mmol of ethylenediamine, and a few drops of acetic acid. (E)-1-(2-thieny)-2-[2-(5-formyl)-thienyl]ethene (1.10 g, 5 mmol) was added slowly at 0° C. The reaction was monitored by TLC until the formyl-containing compound was consumed. Excess sodium borohydride was added and the reaction again was monitored by TLC until the imine intermediate disappeared. The mixture was concentrated under reduced pressure and the residue was treated with 50 ml of EtOAc and 50 ml of 0.1 N HCl. The resulting precipitation was filtered and the filtrate was washed with EtOAc. After combined with the precipitation, the filtrate was treated with 2 N NaOH till pH>12 and then extracted with EtOAc. The organic extract was washed with saturated sodium bicarbonate and brine, and dried with anhydrous MgSO$_4$. After the reaction mixture was filtered and concentrated, 0.74 g of (E)-1-(2-thienyl)-2-[2-{5-[N-(2-hydroxyethyl)aminomethyl]}thienyl]ethene resulted. Recrystallization with n-hexane afforded 0.72 g of the desired product. (E)-1-(2-thienyl)-2-[2-{5-[N-(2-hydroxyethyl)aminomethyl]}thienyl]ethene (mp 104~105° C.): $^1$H NMR (CD$_3$OD): δ2.71~2.75 (m, 2H), 2.83~2.88 (m, 2H), 3.83 (s, 2H), 6.75 (d, 1H, J=3.3 Hz), 6.79~6.94 (m, 5H), 7.14 (d, 1H, J=4.2 Hz). MS (m/z): 264 (M$^+$, 12.4), 220 (33.20), 205 (100), 171 (15.63), 97 (24.61), 85 (16.80), 83 (29.30), 73 (24.80), 71 (28.71), 69 (34.57). IR (KBr, cm$^{-1}$): 3318, 3274, 3223, 3101, 3066, 3016, 2927, 1616, 1111.

EXAMPLE 8

(E)-1-(2-thienyl)-2-(2-[5-{N-[N-(2-hydroxyethyl)aminoethyl]aminoethyl}]thienyl)ethene In a 100-ml flask was placed 30 ml of methanol, 10 mmol of 2-(2-aminoethylamino)ethanol and a few drops of acetic acid. (E)-1-(2-thieny)-2-[2-(5-formyl)-thienyl]ethene (1.10 g, 5 mmol) was added slowly at r.t. The reaction was monitored by TLC until the formyl-containing compound was consumed. Excess sodium borohydride was added and the reaction again was monitored by TLC until the imine intermediate disappeared. The mixture was concentrated under reduced pressure and the residue was treated with 50 ml of EtOAc and 50 ml of 0.1 N HCl. The resulting precipitation was filtered and the filtrate was washed with EtOAc. After combined with the precipitation, the filtrate was treated with 2 N NaOH till pH>12 and then extracted with EtOAc. The organic extract was washed with saturated sodium bicarbonate and brine, and dried with anhydrous MgSO$_4$. After the reaction mixture was filtered and concentrated, 1.36 g of (E)-1-(2-thienyl)-2-(2-(5-[N-2-hydroxyethyl)-aminomethyl))thienyl)ethene was obtained. Recrystallization with n-hexane afforded 1.29 g of the desired product. (E)-1-(2-thienyl)-2-[2-{5-[N-2-hydroxyethyl)-aminomethyl]}-thienyl)ethene (mp 51~52° C.): $^1$H NMR (CDCl$_3$): δ2.27 (br, 3H), 2.73~2.80 (m, 6H), 3.62~3.65 (m, 2H), 3.93 (s, 2H), 6.78 (d, 1H, J=3.9 Hz), 6.85 (d, 1H, J=3.3 Hz), 6.96~7.01 (m, 4H), 7.16 (t, 1H). MS (m/z: 308 (M$^+$, 6.97), 233 (21.52), 220 (24.59), 205 (100), 171 (12.55), 74 (55.74). IR (KBr, cm$^{-1}$): 3174, 3108, 2916, 2831.

EXAMPLE 9

Synthesis of 1-(2-(5-formyl-furyl)-4-(2-(5-formylthienyl)) benzene (i) In a 2-neck flask was placed 1,4-dibromobenzene (13.5 g, 57 mmol) with catalyst Pd(PPh$_3$)$_4$ and added 30 mL of benzene and 6 mL of 2 M Na$_2$CO$_3$ aqueous solution. The mixture was then added a methanol solution of dihydroxy-(2-(5-formyl-furyl))borane (2 g, 14 mmol) and heated at reflux for 12 hrs. TLC showed 2 fluorescent spots. The less polar spot was identified as desired dimer product. The mixture was extracted with ether. The combined ether extracts were dried with anhydrous MGSO$_4$ and concentrated. Chromatograph yielded 30% of 1-bromo-4-(2-formylfuryl)benzene. $^1$H NMR (CDCl$_3$, 200 MHz): δ6.82 (d, J=3.8 Hz, 1H), 7.29 (d, J=3.8 Hz, 1H), 7.45~7.72 (AA'BB', 4H), 9.64 (s, 1H).

(ii) In a 2-neck flask was placed 1-bromo-4-(2-(5-formylfuryl))benzene (0.25 g, 1 mmol), 2-(diethoxymethyl)-5-(tributylstannyl)thiophene (0.95 g, 2 mmol), and 5 mol % of catalyst Pd(PPh$_3$)$_2$Cl$_2$. After 50 mL of THF was added, the mixture was heated at reflux for 12 hrs. The reaction was quenched with ammonium hydroxide solution and extracted with ether. The combined ether extracts were dried with anhydrous MGSO$_4$ and concentrated to yield 50% of the desired product. $^1$H NMR (CDCl$_3$, 300 MHz): δ6.89 (d, J=3.7 Hz, 1H), 7.32 (d, J=3.7 Hz, 1H), 7.46 (d, J=3.9 Hz, 1H), 7.70–7.93 (m, 5H), 9.66 (s, 1H), 9.89 (s, 1H).

EXAMPLE 10

Synthesis of 1,4-bis[2-(5-formyl)thienyl]benzene

In a 2-neck flask was placed 0.236 g (1 mmol) of 1,4-dibromobenzene, 0.95 g (2 mmol) of 2-(diethoxymethyl)-5-(tributylstannyl)thiophene, and 5 mol % of catalyst Pd(PPh$_3$)$_2$Cl$_2$. After 50 mL of THF was added, the mixture was heated at reflux for 12 hrs. The reaction was quenched with ammonium hydroxide solution and extracted with ether. The combined ether extracts were dried with anhydrous MgSO$_4$ and concentrated to yield 0.24 g (80% yield) of the desired product (mp>268° C., decomposed). $^1$H NMR (CDCl$_3$, 300 MHz): δ7.45 (d, J=4.0 Hz, 2H), 7.72 (s, 4H), 7.75 (d, J=4.0 Hz, 2H), 9.89 (s, 2H); MS (m/z): 297 (M-1, 42), 268 (2), 225 (17), 222 (8), 187 (8), 149 (7), 115 (13), 45 (100).

EXAMPLE 11

Synthesis of 1,4-bis(2-(5-hydroxymethyl)thienyl)benzene

Excess NaBH$_4$ was added to a solution of 1,4-bis(2-(5-formyl)thienyl)benzene (100 mg) in ethanol (50 mL) under N$_2$ at r.t. The reaction was stirred for 4 hrs and was quenched with aqueous ammonium chloride afterwards and extracted with ether. The combined ether extracts were dried with anhydrous MgSO$_4$ and concentrated to yield 90% (91 mg) of the desired product (mp>300° C.). $^1$H NMR (DMSO-d$_6$, 200 MHz): δ4.62 (s, 4H), 6.95 (d, J=3.5 Hz, 2H), 7.36 (d, J=3.5 Hz, 2H), 7.62 (s, 4H); MS (m/z): 301 (M-1, 1), 256 (1), 203 (2), 173 (1), 149 (3), 129 (3), 45 (100).

EXAMPLE 12

Screening of compounds for antitumor activity

The cytotoxic activity of the polyaryl compounds are measured utilizing the cytotoxicity against a panel of sixty one different NCI human tumor cell lines.

The sixty one tumor cell lines used to test the antitumor activity of the above-listed polyaryl compounds are listed below:

Leukemia
  CCRF-CEM, HL-60 (TB), K-562, MOLT-4, RPMI-8226, and SR.
Lung Cancer
  A549/ATCC, EKVX, HOP-62, HOP-92, NCI-H226, NCI-H23, NCI-H322M, NCI-H460, and NCI-H522.
Colon Cancer
  COLO 205, HCC-2998, HCT-116, HCT-15, HT-29, KM-12, and SW-620.
CNS Cancer
  SF-268, SF-295, SF-539, SNB-19, SNB-75, and U-251.
Melanoma
  LOX-IMVI, MALME-3M, M-14, SK-MEL-2, SK-MEL-28, SK-MEL-5, UACC-257, and UACC-62.
Ovarian Cancer
  IGR-OVI, OVCAR-3, OVCAR-4, OVCAR-5, OVCAR-8, and SK-OV-3.
Renal Cancer
  786-0, A-498, ACHN, CAKI-1, RXF-393, RXF-631, SN12C, TK-10, and U0-31.
Prostate Cancer
  PC-3 and DU-145.
Breast Cancer
  MCF 7, MCF7/ADR-RES, MDA-MB-231/ATCC, HS578T, MDA-MB-435, MDA-N, BT-549, and T-47D.

This NCI antitumor activity screening assay provides data regarding the general cytotoxicity of an individual compound. In particular, this type of assay is useful in identifying compounds which have enhanced cytotoxic activity against slow growing tumors as compared to faster growing tumor cells such as leukemia tumor cell lines. The identification of such compounds is critical since previously identified antitumor agents have low cytotoxic activity against slower growing tumors.

The antitumor cytotoxicity of the polyaryl compounds tested in the in vitro assays was measured by a microculture assay using either 3-(4,5-dimethylthiazol-2-yl)-2,5-diphenyltetrazolium bromide ("MTT"). This assay has an advantage over in vivo assay in that results are obtained within a week as opposed to several months. The assay was carried out in 96-well microtiter plates. The MTT assay is based on the production of a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbout, J. G. Mayo, R. H. Shoemaker and M. R. Boyd, Cancer Res., 48, 589, 1988]. Thus, only live cells are stained and can be measured at 570 nm. Antitumor cytotoxicity is reported as $IC_{50}$, effect drug dose at which cell growth is retarded to 50% of control culture of tumor cells.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of the formula:

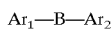

wherein $Ar_1$ is thienyl;

B is

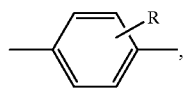

—CH=CH—, or —C—C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where each R$_1$, independently, is H, alkyl, or acyl; and each of R$_2$ and R$_3$, independently, is H, alkyl, hydroxyalkyl, or aminoalkyl; and $Ar_2$ is substituted thienyl, in which each substituent of said substituted thienyl, independently, is amido, nitrile, nitro, cyano, acetal, ketal, oxyalkyl, aminoalkyl, haloalkyl, iminoalkyl, acid halide, aminoalkylaminoalkyl, aminoalkylaminoalkylamino, hydroxyalkylaminoalkyl, or hydroxyalkylaminoalkylaminoalkyl; or a salt thereof.

2. The compound of claim 1, wherein B is

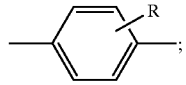

or a salt thereof.

3. The compound of claim 2, wherein each substituent of said substituted thienyl, independently, is oxyalkyl, aminoalkyl, haloalkyl, hydroxyalkylaminoalkyl, or hydroxyalkylaminoalkylaminoalkyl; or a salt thereof.

4. The compound of claim 1, wherein B is —CH=CH—.

5. The compound of claim 4, wherein each substituent of said substituted thienyl, independently, is oxyalkyl, aminoalkyl, haloalkyl, hydroxyalkylaminoalkyl, or hydroxyalkylaminoalkylaminoalkyl; or a salt thereof.

6. The compound of claim 1, wherein B is —C≡C—.

7. The compound of claim 6, wherein each substituent of said substituted thienyl, independently, is oxyalkyl, aminoalkyl, haloalkyl, hydroxyalkylaminoalkyl, or hydroxyalkylaminoalkylaminoalkyl; or a salt thereof.

8. A compound of the formula:

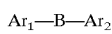

wherein $Ar_1$ is substituted thienyl, in which each substituent of said substituted thienyl, independently, is aldehyde, acyl, ester, carboxyl, amido, nitrile, nitro, cyano, acetal, ketal, oxyalkyl, aminoalkyl, hydroxyalkyl, haloalkyl, iminoalkyl, acid halide, aminoalkylaminoalkyl, aminoalkylaminoalkylamino, hydroxyalkylaminoalkyl, or hydroxyalkylaminoalkylaminoalkyl;

B is

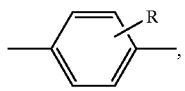

—C=CH—, or —C C—, in which R is H, alkyl, hydroxy, alkoxy, ester, aldehyde, hydroxyalkyl, aminoalkyl, carboxyl, —CH(OR$_1$)$_2$, or NR$_2$R$_3$, where R$_1$ is H, alkyl, or acyl; and each of R$_2$ and R$_3$, independently, is H, alkyl, hydroxyalkyl, or aminoalkyl; and Ar$_2$ is; in which A is sulfur; X is carboxyl, amido, nitrile, nitro, cyano, acetal, ketal, oxyalkyl, aminoalkyl, hydroxyalkyl, haloalkyl, acid halide, aminoalkylaminoalkyl, aminoalkylaminoalkylamino, hydroxyalkylaminoalkyl, or hydroxyalkylaminoalkylaminoalkyl; Y is aldehyde, acyl, ester, carboxyl, amido, nitrile, nitro, cyano, acetal, ketal, oxyalkyl, aminoalkyl, hydroxyalkyl, haloalkyl, iminoalkyl, acid halide, aminoalkylaminoalkyl, aminoalkylaminoalkylamino, hydroxyalkylaminoalkyl, or hydroxyalkylaminoalkylaminoalkyl; Z is acyl, ester, carboxyl, amido, nitrile, nitro, cyano, acetal, ketal, oxyalkyl, aminoalkyl, hydroxyalkyl, haloalkyl, iminoalkyl, acid halide, aminoalkylaminoalkyl, hydroxyalkylaminoalkyl, or hydroxyalkylaminoalkylaminoalkyl; or a salt thereof.

9. The compound of claim 8, wherein B is

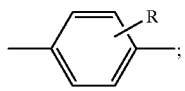

or a salt thereof.

10. The compound of claim 9, wherein each substituent of Ar$_1$, independently, is aldehyde, oxyalkyl, hydroxyalkyl, acyl, or ester; or a salt thereof.

11. The compound of claim 10, wherein Ar$_2$ is

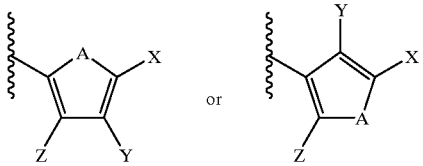

in which each of X and Z, independently, is hydroxyalkyl; Y is aldehyde or hydroxyalkyl; or a salt thereof.

12. The compound of claim 11, wherein each substituent of Ar$_1$, independently, is aldehyde or hydroxyalkyl; or a salt thereof.

13. The compound of claim 8, wherein B is —C=CH—.

14. The compound of claim 13, wherein each substituent of Ar$_1$, independently, is aldehyde, oxyalkyl, hydroxyalkyl, acyl, or ester; or a salt thereof.

15. The compound of claim 14, wherein Ar$_2$ is

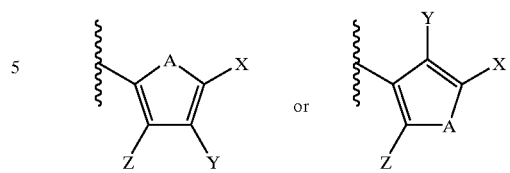

in which each of X and Z, independently, is hydroxyalkyl; Y is aldehyde, or hydroxyalkyl; or a salt thereof.

16. The compound of claim 15, wherein each substituent of Ar$_1$, independently, is aldehyde, or hydroxyalkyl; or a salt thereof.

17. The compound of claim 8, wherein B is —C≡C—.

18. The compound of claim 17, wherein each substituent of Ar$_1$, independently, is aldehyde, oxyalkyl, hydroxyalkyl, acyl, or ester; or a salt thereof.

19. The compound of claim 18, wherein Ar$_2$ is

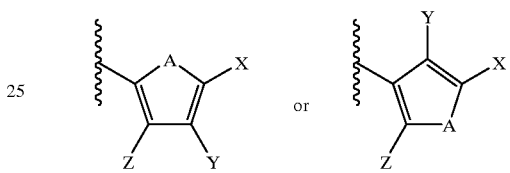

in which each of X and Z, independently, is hydroxyalkyl; Y is aldehyde or hydroxyalkyl; or a salt thereof.

20. The compound of claim 19, wherein each substituent of Ar$_1$, independently, is aldehyde or hydroxyalkyl; or a salt thereof.

21. An asymmetric compound of the formula

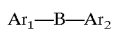

wherein
each of Ar$_1$ and Ar$_2$, independently, is substituted thienyl, in which each substituent of said substituted thienyl, independently, is acetal, ketal, oxyalkyl, hydroxyalkyl, aminoalkyl, iminoalkyl, acyl, carboxyl, ester, amide, acid halide, nitrile, or hydroxyalkylaminoalkylaminoalkyl; and
B is

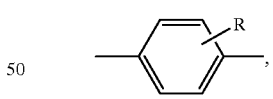

—CH=CH—, or —C C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where R$_1$ is H, alkyl, or acyl; each of R$_2$ and R$_3$, independently, is H, alkyl, hydroxyalkyl, or aminoalkyl; or a salt thereof.

22. The compound of claim 21, wherein each substituent of Ar$_1$ and Ar$_2$, independently, is aldehyde, oxyalkyl, hydroxyalkyl, acyl, or ester; or a salt thereof.

23. The compound of claim 22, wherein each substituent of Ar$_1$ and Ar$_2$, independently, is aldehyde or hydroxyalkyl; or a salt thereof.

24. A pharmaceutical composition, comprising an effective amount of a compound of the following formula:

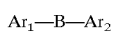

wherein each of $Ar_1$ and $Ar_2$, independently, is thienyl or substituted thienyl, in which each substituent of substituted thienyl, independently, is aldehyde, acyl, ester, carboxyl, amido, nitrile, nitro, cyano, acetal, ketal, oxyalkyl, aminoalkyl, hydroxyalkyl, haloalkyl, iminoalkyl, acid halide, aminoalkylaminoalkyl, aminoalkylaminoalkylamino, hydroxyalkylaminoalkyl, or hydroxyalkylaminoalkylaminoalkyl; and B is

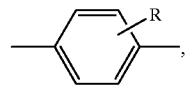

—C=CH—, or —C C—, in which R is H, alkyl, hydroxyl, alkoxy, ester, aldehyde, hydroxyalkyl, aminoalkyl, carboxyl, —CH(OR$_1$)$_2$, or NR$_2$R$_3$, where R$_1$ is H, alkyl, or acyl; and each of R$_2$ and R$_3$, independently, is H, alkyl, hydroxyalkyl, or aminoalkyl;

and a pharmaceutical acceptable carrier thereof.

25. The composition of claim 24, wherein each substituent of $Ar_1$ and $Ar_2$, independently, is aldehyde or hydroxyalkyl.

* * * * *